(12) United States Patent
Tiemens

(10) Patent No.: US 8,061,472 B2
(45) Date of Patent: Nov. 22, 2011

(54) NON-ROLL FOAM EARTIP

(75) Inventor: Jim Tiemens, Laguna Niguel, CA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 0 days.

(21) Appl. No.: 12/792,891

(22) Filed: Jun. 3, 2010

(65) Prior Publication Data

US 2010/0307861 A1    Dec. 9, 2010

Related U.S. Application Data

(60) Provisional application No. 61/183,872, filed on Jun. 3, 2009.

(51) Int. Cl.
*A61B 7/02* (2006.01)
(52) U.S. Cl. .................................. 181/135; 264/46.9
(58) Field of Classification Search .................. 181/135; 264/46.9
See application file for complete search history.

(56) References Cited

U.S. PATENT DOCUMENTS

| | | | |
|---|---|---|---|
| 4,053,051 A | 10/1977 | Brinkhoff | |
| 4,434,794 A * | 3/1984 | Leight | 128/867 |
| 4,774,938 A | 10/1988 | Leight | |
| 5,188,123 A | 2/1993 | Gardner, Jr. | |
| 5,203,352 A | 4/1993 | Gardner, Jr. | |
| D375,550 S | 11/1996 | Esler et al. | |
| D375,551 S | 11/1996 | Esler et al. | |
| 5,573,015 A | 11/1996 | Williams | |
| 5,792,998 A | 8/1998 | Gardner, Jr. et al. | |
| 5,799,658 A * | 9/1998 | Falco | 128/864 |
| D402,752 S | 12/1998 | Falco | |
| D403,062 S | 12/1998 | Dix | |
| D405,173 S | 2/1999 | Falco | |
| D409,743 S | 5/1999 | Falco et al. | |
| D413,379 S | 8/1999 | Leight | |
| 5,957,136 A | 9/1999 | Magidson et al. | |
| 5,988,313 A * | 11/1999 | H.ang.kansson | 181/135 |
| 6,006,857 A * | 12/1999 | Leight et al. | 181/135 |
| D427,304 S | 6/2000 | Magidson et al. | |
| 6,241,042 B1 * | 6/2001 | Falco | 181/135 |
| 6,425,398 B1 | 7/2002 | Hirshfeld | |

(Continued)

FOREIGN PATENT DOCUMENTS

WO    9200049 A1    1/1992

(Continued)

OTHER PUBLICATIONS

PCT/US2010/037284, International Search Report and Written Opinion dated Feb. 21, 2011; 7 pages.

*Primary Examiner* — Forrest M Phillips
(74) *Attorney, Agent, or Firm* — Conley Rose, P.C.; Kristin Jordan Harkins

(57) ABSTRACT

Embodiments disclose a non-roll foam EarTip that may provide for fingertip press-in insertion, improved comfort, simplicity of use, flatter attenuation and/or improved hygienic properties, by way of non-exclusive example. A hollow foam body typically encompasses a shorter stem of more rigid material, and in some embodiments the foam body has a tighter skin on the inner and outer surfaces. In some embodiment, the EarTip is an earplug formed of polyurethane foam with a dense skin on the inner and outer surfaces of the hollow body, and having a plurality of splines in the cavity.

25 Claims, 12 Drawing Sheets

U.S. PATENT DOCUMENTS

| | | |
|---|---|---|
| D466,995 S | 12/2002 | Knauer et al. |
| D471,625 S | 3/2003 | Falco |
| D472,627 S | 4/2003 | Falco |
| 6,568,394 B2 | 5/2003 | Falco |
| D478,658 S | 8/2003 | Falco |
| D481,118 S | 10/2003 | Doty et al. |
| 6,659,103 B2 * | 12/2003 | Tiemens ............... 128/864 |
| 6,695,093 B1 | 2/2004 | Falco |
| D492,766 S | 7/2004 | Falco |
| D492,767 S | 7/2004 | Knauer et al. |
| D492,768 S | 7/2004 | Knauer et al. |
| D496,722 S | 9/2004 | Falco et al. |
| D512,141 S | 11/2005 | Mishkin et al. |
| 6,981,504 B2 * | 1/2006 | Jenkins, Jr. ............ 128/864 |
| D524,937 S | 7/2006 | Doty et al. |
| 7,096,872 B2 * | 8/2006 | Ligon et al. ............ 128/864 |
| D528,204 S | 9/2006 | Doty et al. |
| D529,169 S | 9/2006 | Ryan |
| 7,107,993 B2 | 9/2006 | Magidson |
| D536,089 S | 1/2007 | Magidson et al. |
| D538,924 S | 3/2007 | Doty |
| D539,415 S | 3/2007 | Fleming |
| 7,192,544 B2 * | 3/2007 | Jenkins, Jr. et al. ......... 264/46.4 |
| 7,210,484 B1 | 5/2007 | Tiemens et |
| 7,305,992 B2 | 12/2007 | Fleming |
| D560,792 S | 1/2008 | Miller |
| 7,314,047 B2 | 1/2008 | Falco |
| D577,812 S | 9/2008 | Zwart |
| 7,464,786 B2 | 12/2008 | Falco et al. |
| 7,475,686 B2 * | 1/2009 | Knauer et al. ............ 128/864 |
| 7,510,046 B2 | 3/2009 | Doty |
| 7,537,011 B2 | 5/2009 | Falco |
| 7,600,604 B2 * | 10/2009 | Babcock et al. ............ 181/130 |
| 7,697,706 B2 | 4/2010 | Doty |
| 7,727,433 B2 | 6/2010 | Knauer et al. |
| 7,743,771 B2 | 6/2010 | Falco |
| 2003/0051939 A1 * | 3/2003 | Werblud ................ 181/131 |
| 2004/0045558 A1 | 3/2004 | Taylor et al. |
| 2005/0056289 A1 | 3/2005 | Jenkins, Jr. et al. |
| 2006/0162992 A1 | 7/2006 | Seville |
| 2007/0221232 A1 | 9/2007 | Jenkins |

FOREIGN PATENT DOCUMENTS

WO     WO 03013390 A2     2/2003

* cited by examiner

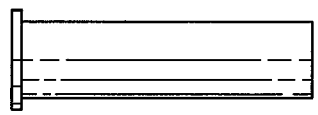
FIG. 12J  FIG. 12K  FIG. 12L
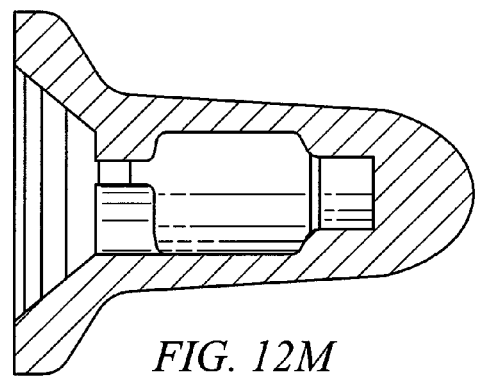
FIG. 12M
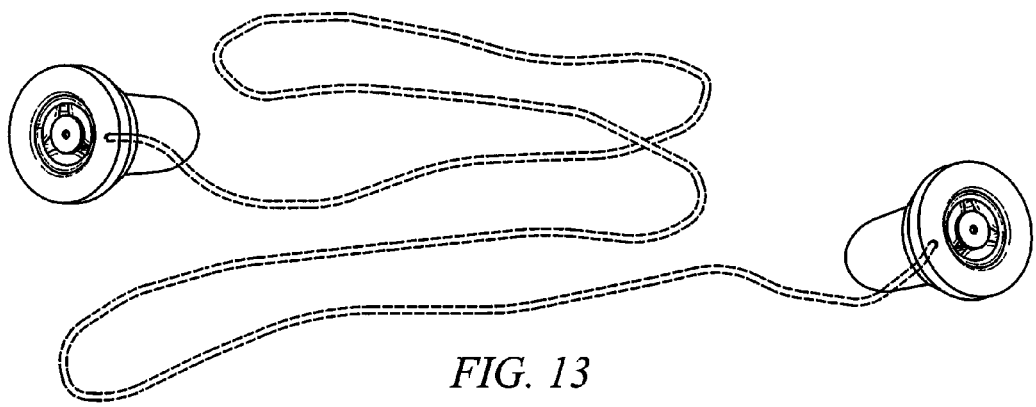
FIG. 13

NON-ROLL FOAM EARTIP

CROSS-REFERENCE TO RELATED APPLICATIONS

This application is related to and claims priority under 35 USC §119 to co-pending U.S. Provisional Patent Application Ser. No. 61/183,872 entitled "Non-Roll Foam Earplug," filed Jun. 3, 2009, which is hereby fully incorporated by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

Disclosed embodiments may relate generally to hearing protection, and more specifically to non-rolldown, press-in earplugs. Embodiments may also relate to other EarTips, especially those having a sealing and/or sound attenuation section.

BACKGROUND

In very noisy environments, workers often wear earplugs or other hearing protection designed with high noise blocking capabilities (such as a noise reduction rating or NRR at or around 33). But in moderately noisy environments, a lower level of hearing protection (with NRR in a range of 20 to 30, by way of example) may be sufficient to effectively offer protection from background noise in the workplace. Such lower NRR levels can also be useful in moderately noisy environments, because they may allow workers to have some ability to hear useful, non-dangerous sounds, while still being adequately protected from long-term background noise that could lead to hearing damage. By way of example, it may be useful for workers to be able to hear a supervisor or co-worker shouting over the background noise, allowing for some verbal communication in the moderately noisy workplace which may improve work efficiency and workplace safety.

Allowing such useful sounds through to the user, while blocking out damaging levels of sound exposure in accordance with OSHA or other health regulations, may also help workers be able to leave the hearing protection in place throughout the day (since some necessary communication may be possible without the need to remove the earplugs). This may further help to ensure that the workers are adequately protected from damaging workplace background noise exposure, since workers will not need to remove the earplugs in order to communicate (which would expose them to damaging levels of sound for a period of time without any hearing protection), and since workers will not have to remove and replace the earplugs throughout the workday as they try to communicate (which could lead to improper insertion of the earplug in a manner that does not offer sufficient protection, since the earplugs would then be inserted in less than ideal circumstances). It also may be important to ensure that hearing protection is not so complete that workers would be unable to hear alarms or other audible warning signals.

Applicant has also found that, while press-in (non-rolldown) earplugs may be considered simpler to insert by many users and may typically be less prone to soiling (since they are handled less by users), comfort concerns may need to be addressed; the stiffness often needed for effective push-in insertion may cause discomfort. Applicant has also found that standard press-in type earplugs with extended handles (in which the more rigid handles protrude from the foam earplug) may be unsatisfactory in several ways. For example, the handles tend to produce a level of discomfort when the handle contacts the ear canal wall and/or comes into direct contact with external portions of the concha. Indeed, the extended handles may also come into contact with external objects as they jut out from the user's ear, making their use difficult in conjunction with some hats, helmets, glasses, etc, and creating a safety risk since exterior objects could inadvertently contact the handle and drive the earplug too deep within the ear canal. Additionally, extended handles tend to produce a level of resonance that may negatively affect the sound attenuating properties of these earplugs (with the handles acting similarly to a tuning fork). Thus, Applicant has considered techniques that may improve comfort while allowing for effective insertion of the earplug in a user's ear canal.

SUMMARY

The present invention is typically used in hearing protection applications, providing sufficient NRR to protect those in moderately noisy environments while also allowing some sound through to the user. The applicant has realized a need for an earplug that could provide sufficient hearing protection for a moderately noisy environment, while also allowing for some verbal communication. Effective hearing protection for moderately noisy environments might preferably have a "flatter" response, in that the percentage of noise blocked would vary only slightly with the frequency of sounds to which the user would typically be exposed. Improved sound attenuation at the difficult lower frequencies would likely be especially beneficial, since this would provide good protection in a moderately noisy environment while still allowing the user to hear and understand those speaking/shouting to him (such as a co-worker or supervisor). Applicant has further realized a need to improve the comfort of press-in (non-rolldown) earplugs, while also ensuring effective and easy insertion.

In the preferred embodiments, such features as moderate hearing protection while allowing for some verbal communication, flatter than normal attenuation across the range of typical frequencies, and/or improved comfort might also be combined with one or more other desirable properties such as: an earplug that is easy to insert, without the need for roll-down, manufactured with a material formulated to produce an enhanced resistance to soiling and an ability to be wiped clean to allow for longer term usage. It would also be highly desirable to use materials and components that allow for a lower cost method of manufacture. Preferably, the earplugs would include a hollow body or shell of sound attenuating foam material, and a flexible stem of a material more rigid than that used for the body shell, with the stem possibly press-fit but not attached into the core of the body (so that it can slide along the central axis to deform the sound attenuating body to aid in insertion). Alternatively, the stem could be bonded to at least a portion of the body shell.

In one embodiment, the hearing protection device would comprise a hollow body formed of sound attenuating foam having outside walls (surface/shape) adapted to directly contact the surface of an ear canal, a substantially occluded or closed front end, an open rear end, an inside surface, and a central axis; and a stem of flexible material that is stiffer than the body, located along the central axis of the body; wherein the stem comprises a hollow tube. The substantially occluded front end of the hollow body may be completely closed off in some embodiments (typically having a closed parabolic shaped tip when used as an earplug, for example), or it may have a small opening allowing for sound transmission into the ear canal (as from the sound tube of a sound transmission device in the instance of an ear tip, for example). The foam might be any foam plastic material. Typically, foam plastic materials with sound attenuating properties would be used, since the shell is often used to seal a user's ear canal from an external sound environment. Examples might include polyurethane or PVC foam. Preferred embodiments may use viscoelastic foam, with latex-modified polyurethane being a typical example. In an aspect, the stem might include at least one slit at the front end of the stem, and/or a flange at the rear end of the stem. The stem could also optionally be crimped along its length. Further, the hollow tube of the stem may be at least partially filled with sound attenuating material. The sound attenuating foam of the hollow body may be polyurethane foam, the flexible material of the stem may be thermoplastic polyurethane, and the hollow body may be chemically bonded to at least the front end of the stem. In an alternative variant, the stem may be composed of a thermoplastic elastomer.

Another embodiment may be a method of forming an Ear-Tip comprising the steps of extruding a tubular stem with a front end, a rear end, and a cavity therethrough; placing the stem in a mold shaped to form a hollow shell body having outside walls adapted to directly contact the surface of an ear canal and an inside surface; and providing foamable materials in the mold such that the foamable materials may also enter the cavity of the tubular stem. The stem may be placed in the mold so that it will be located approximately on the central axis of the hollow shell body. The stem and the hollow shell body may be formed of homologous materials, such that a chemical bond forms between the hollow shell body and at least the front end of the stem. In one aspect, the stem may be formed of TPU and the hollow shell body may be formed of foam polyurethane (FPU). The method may further comprise forming a flange at the rear end of the stem, cutting at least one slit in the front end of the stem, and/or crimping the hollow stem at least once along its length. In an aspect, the resulting foam hollow shell body may comprise a dense skin on the inside and outside surfaces.

In another embodiment, the body would provide flatter sound attenuation (with approximately constant attenuation over a wide range of audible sound frequencies, such as 125 Hz to 4,000 Hz by way of non-exclusive example), and/or might by way of example offer improved attenuation at lower frequencies. In another possible embodiment, the shell body might be formed of an open cell foam having a denser skin on the inner and/or outer surfaces of the shell. Preferably, the body could be of a reacted mixture of polyurethane foam introduced into a closed mold.

In one aspect, the present disclosure is directed to a hearing protection device, such as an earplug by way of example, comprising a hollow body having outside walls (surface) adapted to directly contact the surface of an ear canal, a closed or occluded front end, an open rear end, an inside surface, and a central axis; and a stem of flexible material that is stiffer than the body, slidably located along the central axis of the body; wherein the hollow body is composed of a sound attenuating material that provides flat sound attenuation. In one embodiment, the hollowness of the body forms a cavity, at least a portion of the stem is located in the cavity (with the remainder of the stem typically located in the front nose portion of the hollow shell body), and/or the body further comprises a plurality of splines projecting into the cavity and supporting the stem in place approximately along the central axis within the cavity (such that portions of the inside surface of the hollow shell body project into the cavity, forming a cavity with a more complex shape). In another embodiment, the stem is further supported in place by the presence of a narrow neck section that additionally acts as a sound attenuation baffle. In another embodiment, the sound attenuating material is an open cell foam. The open cell foam forming the hollow body may also have a denser skin on the inside and/or outside surface. The open cell foam may also provide improved attenuation at lower frequencies, and/or the body shell may provide sound attenuation that is approximately constant over a range of frequencies between about 125 Hz and about 4,000 Hz. In an embodiment of the present invention, the outside walls of the body may have a thickness varying between about 0.04 inches and about 0.125 inches.

In another embodiment, the sound attenuating material is molded polyurethane foam, and might typically be latex-modified polyurethane foam. The polyurethane foam may be formed by foaming reactants in a mold for forming the inner surface as well as an outer surface of the body. In an embodiment, the polyurethane foam body may comprise a dense skin on the inside and/or outside surface. The skin may have a thickness on the order of from one-twentieth millimeter to 0.5 millimeter, and be substantially continuous, and the polyurethane foam body may also have open cells of varying size, with the average cross-sectional area of cells being less near the inner (and/or outer) surface than at the middle of the cross-section of the outside walls. Embodiments may have more open cells towards the middle of the cross-section of the walls of the hollow shell body, with cells at the inner and outer surfaces typically being primarily closed cells that may form a tight cell structure at the surfaces that may create a more hygienic skin.

In some instances, the polyurethane foam may be molded under a pressure of at least about 0.5 psi in a closed mold. And in some embodiments, the polyurethane foam provides improved attenuation at lower frequencies, such that the body may provide sound attenuation that is approximately constant over a range of frequencies between about 125 Hz and about 4,000 Hz. In other embodiments, the splines may be separated around the inside surface/circumference of the hollow body by gaps, with the gaps allowing sufficient sound penetration through the body to allow for some verbal communication to penetrate (and providing moderate levels of sound protection).

In yet another embodiment, an EarTip device (such as an earplug or ear tip) might comprise a hollow body formed of foam plastic material having an outside surface adapted to contact the surface of an ear canal, a substantially occluded front end, an open rear end, an inside surface and a central axis; and a stem of flexible material that is stiffer than the hollow body, located approximately along the central axis of the hollow body, wherein: the hollow body encompasses a cavity; the stem comprises a front tip and a rear end; the rear end of the stem comprises a flange; the stem is completely contained within the hollow body such that the rear end of the stem does not extend out of the open rear end of the hollow body; the rear end of the stem is inset from the open rear end of the hollow body to form a recess in the rear end of the hollow body adapted to receive a fingertip; the hollow body comprises three or more splines projecting into the cavity and supporting the stem in place approximately along the central axis within the cavity; and the inside and outside surfaces of the hollow body comprise a substantially closed cell skin. In some aspects, the front tip of the stem may be chemically bonded to the hollow body. In other aspects, the front end of the hollow body might comprise a pocket, and the front tip of the stem may be press-fit within the pocket. The stem may comprise a hollow tube and/or the front tip of the stem may comprise at least one slit. In some embodiments, the hollow tube of the stem may be at least partially filled with foam plastic material. Additionally, the stem may be crimped at some midpoint between the front and rear ends, such that the stem is wasp-waisted. And in some embodiments, the front end of the hollow body may comprise a parabola-shaped tip; the foam plastic material of the hollow body may comprise open cell foam; the skin on the inside and outside surfaces of the hollow body may have a thickness on the order of about one-twentieth millimeter, and may be substantially continuous; and/or the hollow body may comprise polyurethane foam and the stem may comprise TPE or TPU.

Still another embodiment might be an EarTip device comprising a hollow body formed of open cell foam having an outside surface adapted to contact the surface of an ear canal, a substantially occluded front end, an open rear end, an inside surface and a central axis; and a stem of flexible material that is stiffer than the hollow body, located approximately along the central axis of the hollow body; wherein: the inside and outside surfaces of the hollow body comprise a substantially closed cell skin. The skin may have a thickness on the order of approximately one-twentieth millimeter, may be denser than the open cell foam forming the remainder of the hollow body, and/or may be substantially continuous. In an aspect, the open cell foam may provide flatter sound attenuation by offering improved attenuation at lower frequencies due to the skin. And in some embodiments, the stem may comprise a front tip and a rear end; the front tip of the stem may be chemically bonded to the hollow body; the rear end of the stem may comprise a flange; the stem may be completely contained within the hollow body such that the rear end of the stem does not extend out of the open rear end of the hollow body; and/or the rear end of the stem may be inset from the open rear end of the hollow body to form a recess in the rear end of the hollow body adapted to receive a fingertip.

In another embodiment, an EarTip device may comprise a hollow body formed of foam plastic material having an outside surface adapted to contact the surface of an ear canal, a substantially occluded front end, an open rear end, an inside surface and a central axis; and a stem of flexible material that is stiffer than the hollow body, located approximately along the central axis of the hollow body; wherein: the stem is shorter than the hollow body; the stem comprises a front tip and a rear end; the rear end of the stem comprises a flange; the stem is completely contained within the hollow body such that the rear end of the stem does not extend out of the open rear end of the hollow body; and the rear end of the stem is inset from the open rear end of the hollow body to form a recess in the rear end of the hollow body adapted to receive a fingertip. The foam plastic material may comprise an open cell latex-modified polyurethane foam, and/or the inside and outside surfaces of the hollow body may comprise a substantially closed cell skin. The stem and the hollow body may be formed of homologous materials, and the stem and the hollow body may be chemically bonded at least at the front tip of the stem. The hollow body may comprise an odd number plurality of splines projecting into the cavity. Further embodiments may comprise a cord having a tip, wherein the tip of the cord is embedded in the foam plastic material of the hollow body to securely attach the cord to the hollow body. And in some aspects, the EarTip may be an earplug. Of course, the embodiments of the invention are discussed in greater detail below, and the scope of the invention is not limited by any such characterization, but extends to the full breadth disclosed in the specification and the claims.

BRIEF DESCRIPTION OF THE DRAWINGS

For a more complete understanding of the present disclosure, and for further details and optional advantages thereof, reference is now made to the accompanying drawings, wherein:

FIGS. 12J-12L are perspective drawings of the stem embodiment for the earplug of FIG. 12A;

FIG. 12M is a cross-section drawing of the earplug hollow body of FIG. 12A;

FIG. 13 is a perspective drawing of an embodiment of a pair of earplugs linked by a cord.

DETAILED DESCRIPTION OF THE INVENTION

Figures 1, 2:
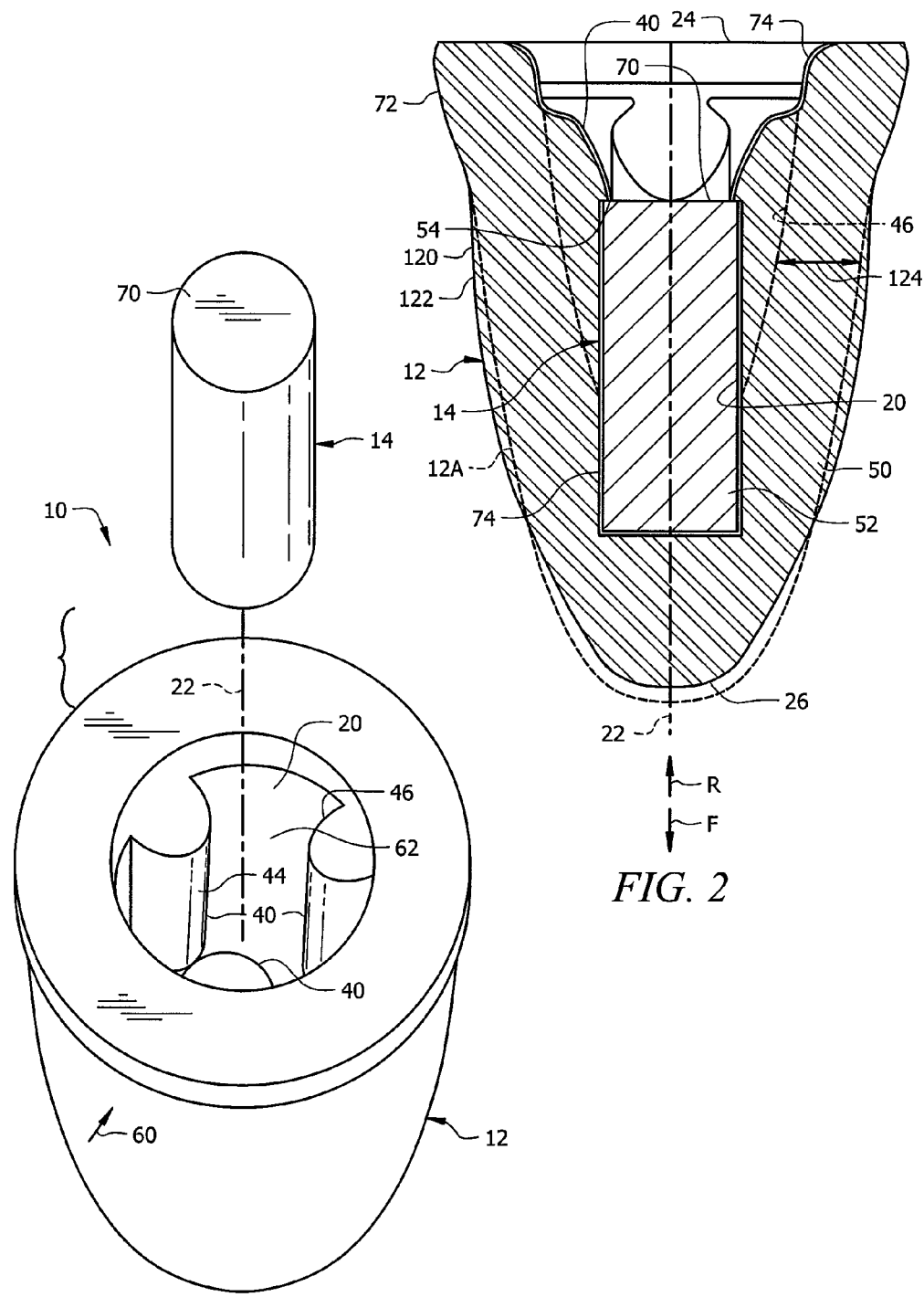
FIG. 1 is a perspective drawing of an embodiment of an earplug.
FIG. 2 is a cross-section drawing of the earplug embodiment of FIG. 1.

Disclosed embodiments may provide for hearing protection in moderately noisy environments (for example effectively protecting from noise in a range of 80 dB to 100 dB), in which NRR between about 20 and 30 are sufficient to adequately protect against hearing damage and/or meet OSHA or other workplace regulations. Further, disclosed embodiments may provide for flatter attenuation of sound across a range of frequencies, so that users in moderately noisy environments may be protected but may also be able to hear some desirable sounds (such as a co-worker or supervisor shouting, by way of non-exclusive example). Additionally, disclosed embodiments may offer reduced soiling and/or the ability to be cleaned, which may allow for increased effective lifespan of usage for disposable earplugs. And disclosed embodiments may offer press-in insertion of the earplugs into a user's ear canal, without the need to roll-down the earplug, while preferably also offering improved comfort and/or sound attenuation. Such press-in insertion allows for quick and easy insertion without requiring a procedure that can be difficult for novices and that can accelerate soiling of the earplug.

The following brief definition of terms shall apply throughout the application:

The term "EarTip" generally refers to either an ear tip for use on a sound transmission device (such as an earbud for a communication headset, a hearing aid, or a portable music device, by way of non-exclusive example), to an earplug for protecting the user's hearing, or to any device comprising such ear tip or earplug elements, with the EarTip typically comprising a resilient portion designed to fit snugly in a user's ear canal;

The term "foam plastic" generally refers to a foam material with resilient recovery properties; foam plastic materials may be low resilient and have slow recovery properties, such that if the foam is compressed and then released, the foam returns back towards its original uncompressed state over a period of time (typically greater than 10 seconds but less than 30 minutes, for example); or foam plastic materials may be resilient and have moderate to fast recovery properties, such that they do not take a long-term set but return back towards the original uncompressed state fairly quickly (typically less than 10 seconds, for example); foam plastic materials may be viscoelastic, and one example of such a viscoelastic foam plastic might be latex-modified polyurethane foam;

The term "sound transmission device" generally refers to any device for transmitting sound into a user's ear canal from an outside source, and by way of nonexclusive example may include personal music devices (such as an IPod™), a communication headset or earpiece, or a hearing aid;

The term "substantially occluded" may refer to an end that is substantially closed off, and may include an end that is completely closed in some embodiments, or the end may comprise a small opening in the end allowing for sound transmission into the ear canal in other embodiments; the term is intended to include a completely closed end and/or an end that comprises an opening or channel therethrough; thus, a substantially occluded end may describe an element for an earplug or an ear tip;

The term "open cell" used when describing foam relates to a foam comprising a plurality of open cells (which for example might have a cell structure with struts but with open windows or ruptured walls); in practice open cell foam may include both open and closed cells, with open cell foam typically having more open cells that a closed cell foam;

The terms "front" and "rear" are used as relative descriptions of the opposing ends of an earplug or other EarTip, with "front" typically describing the end that is directed towards and closest to the ear drum when the EarTip is inserted in a user's ear canal, and "rear" typically describing the end that is directed outward, away from, and furthest from the ear drum;

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment); and If the specification states a component or feature "may," "can," "could," "should," "preferably," "possibly," "typically," "optionally," or "might" (or other such language) be included or has a characteristic, that particular component or feature is not required to be included or to have the characteristic.

FIGS. 1 and 2 show an earplug 10, shaped to fit securely within a user's ear canal in order to effectively seal the ear canal against passage of sound, that includes a hollow body or shell 12 (with a cavity 20) of soft elastomeric material (preferably with a Young's modulus of elasticity of no more than 50,000 psi and/or a 25% IDF (indentation force deflection) value of between about 5 and 30 newtons and perhaps more preferably between 10 and 20 newtons) that is preferably a foam plastic material, and an insertion stem 14 of elastomeric material that is flexible but stiffer than the material of the shell body. The embodiment of FIG. 1 may have a foam shell body with a parabola-shaped front tip. In one embodiment of earplug 10, the shell material has a Shore A stiffness of about 10-30 (and perhaps preferably about 20) and the stem material has a Shore A stiffness of about 60-75. In the embodiment of FIG. 1, the shell 12 is typically constructed of polyurethane foam. Polyurethane foam is not suitable for dip molding, so applicant molds the shell by reacting materials and introducing them into a mold. The mold used for the embodiment of FIG. 1, for example, would have an inner and an outer mold surface, allowing for formation of a hollow shell body 12 of polyurethane foam, and the polyurethane foam would be reaction molded to form shell body 12, typically having a thin, smooth, dense skin on the surfaces. The hollow shell body 12 might be formed of latex-modified polyurethane foam in some embodiments.

The insertion stem 14 may be formed by extruding elastomeric material to form a longitudinal member and then cutting the extrusion into pieces of the desired length of the stem, which can be done at a very low cost. Such extruded stems may be solid, tubular, or have any desired irregular cross section, and, by means of post-extrusion forming, may have modified front, middle, and/or rear portions. By way of non-exclusive examples, the front tip of the extrusion may be made softer and more conformable by post-extrusion processing (perhaps by cutting one or more slits); the front tip could be made more flexible by having thinner walls; the front tip could be formed with corrugations to provide accordion-like flexibility; the stem could be crimped somewhere along its length to alter the sound attenuation, improve flexibility, and/or affect flexibility; and/or a heat-formed finger tip flange may be formed post-extrusion on the rear portion of the stem to provide added comfort and control during fingertip insertion of the earplug 10 into the ear canal. Additionally, the extruded stem 14 may be given a tacky or rougher exterior surface that may aid in its retention within the hollow body shell 12. By way of non-exclusive examples, the exterior surface of the extruded stem may have a surface application finish applied (such as dipping or misting the stem with a substance providing tackiness), or the exterior surface may be roughened up by means of an annular ring cooling nozzle located behind the face of the extruder head. Stems may also be formed using other techniques, such as injection molding, co-extrusion, transfer-molding, reaction-injection molding (RIM), or poured foaming by way of non-exclusive example, and may be straight, tapered, and/or flanged. While the stem shown in the embodiment of FIG. 1 is cylindrical (having a round cross-section), other cross-section shapes are permissible. Indeed, the stem's cross-section may vary along its length as well.

The stem 14 is typically shorter and stiffer than the shell 12 so that it does not extend out beyond the shell 12 but is completely enclosed within the shell 12. Typically, the rear end of the stem (which often has a flange to create a larger surface for fingertip contact, with the flange having a larger outer diameter than the outer diameter for the rest of the length of the stem) may be inset so that the rear end of the stem is recessed within the rear end of the foam shell body. By having the rear end of the stem recessed in the cavity of the hollow shell body, a pocket or recess may be formed to allow for improved fingertip insertion of the earplug (especially when the rear end of the stem has a larger diameter finger tip flange). The stem of FIG. 1 does not serve as a handle (since it is encompassed within the foam shell body and could not be grasped by a user's fingers), but rather may be contacted by a fingertip received in the rear recess. By pushing and optionally twisting the fingertip into the pocket when the earplug is positioned at the ear, a user may simply and effectively press-in insert the earplug of FIG. 1 without the need to roll-down the foam. In the embodiment of FIG. 1, the stem may be held in sliding relationship at or near the central axis of the cavity within the shell 12 of the earplug. By way of example, the stem 14 may be held in axial alignment by a press-fit pocket inside the foam tip and/or a narrow internal neck portion of the foam body (either as an annular baffle, continuous or interrupted splines projecting out from the inside surface of the outside walls of the shell body, or other annular projections). In alternative embodiments, the front tip of the stem may be bonded to the forward (nose) portion of the foam shell. In FIG. 1, the stem 14 is composed of a solid elastomeric material (although other solid materials of sufficient stiffness may also be used). In one embodiment of the earplug of FIG. 1, the shell 12 is formed of foam polyurethane (FPU) and the stem is formed of thermoplastic elastomer urethane (TPU). In another embodiment, the stem is formed of a thermoplastic elastomer (TPE), while the shell is formed of FPU.

FIGS. 1 and 2 show that the shell 12 has a blind passage 20 that lies on the earplug axis 22, the passage having an open rear R end 24 and a closed (occluded) front F end 26. The walls of the passage form a plurality of radially (with respect to the axis) inward projections or splines 40. The insertion stem 14 may be guided in slight axial movement by the radially inner surfaces 44 of the splines. Axially elongated gaps 46 lie between adjacent splines and are unfilled. This allows sound to pass forward from the environment though the gaps 46 between splines with less attenuation. The sound then passes through front portions 50, 52 of the shell and stem with moderate attenuation and into the ear canal of the wearer. The splines also reduce the thickness of the shell walls, so the shell can more easily bend to follow non-straight configurations of a user's ear canal. The level of compliability provided by the hollow shell walls may improve comfort, providing lower expansion pressure in the ear canal, improved navigation of the curvature of the ear canal during insertion, and/or improved adaptability to specific curvature of a user's ear canal. Further, such a thin-walled shell 12 as shown in the embodiment of FIG. 1 structurally allows for the diameter of the earplug 10 to collapse more readily during insertion (when acted upon by the stem 14), improving the earplug's ability to be inserted effectively via fingertip press-in. While any number of splines might be used (or alternatively no splines), there are preferably an odd number of splines, so for any direction of bending perpendicular to the earplug axis, at least one side of the shell has a thin wall without a spline there. This is shown in FIG. 1 where bending to deflect a spline along arrow 60 causes the opposite side of the shell at splineless location 62 to deflect. This configuration of splines and gaps allows for the shell's diameter to readily collapse during insertion, providing a compliant earplug that may ease and simplify the insertion process. The range of attenuation may also be modified by altering the length of the foam shell (so more of the ear canal is plugged), the size of the nose of the foam shell, the diameter of the earplug, the thickness of the shell walls, the size and shape of the cavity and/or the interaction between the cavity walls of the foam shell body and the stem, for example.

FIG. 2 shows that this embodiment has an interference fit between the stem splines 40 and the stem 14 of an imaginary cylinder (or other similar shape). As a result, the stem "digs" radially outward into the shell material and the shell acquires a shoulder 54 that resists removal of the stem. When the earplug is installed, a user presses forwardly against the rear end 70 of the stem, while the rear end 72 of the shell is held against forward movement by the entrance to the ear canal. This elongates and narrows the shell, as to orientation 12A, which makes it easier to install the earplug. When forward pressure is no longer applied to the rear end of the stem, the shell returns toward its original orientation and the stem abuts the shell shoulder 54, resulting in a snug fit of the earplug in the user's ear canal that effectively blocks sound to attenuate moderate levels of noise into a safe range. So, when the stem is pushed (by a user's fingertip being inserted into the open end of the shell), its front end pushes on the front of the shell, elongating the shell and thereby reducing (collapsing) its diameter to facilitate shell insertion into the ear canal. With an optional additional slight twisting motion of the fingertip on the stem, there may be a further reduction in the shell diameter, allowing for still easier insertion. When the pushing force stops, the shell can expand its diameter back towards its original, unflexed diameter, thereby snugly lodging to seal the ear canal. In the course of pressing and releasing the stem during insertion, the stem of this embodiment may slide within the shell. And to facilitate the ability of the shell to collapse its diameter during insertion, the stem's diameter is significantly less than the outer diameter of the shell, providing a gap space (typically the portion of the cavity between the stem and the inside surface of the hollow shell body walls) that permits the reduction of the shell diameter.

As mentioned above, the shell 12 is typically manufactured by molding both its inside and outside surfaces in a mold, and by using polyurethane foam for the shell. More specifically, this embodiment of the earplug is typically formed using a mold shaped to produce a thin, hollow bodied shell with splines (projecting into the cavity), with urethane foam material molded therein to form shell 12. This may be accomplished by mixing the foam materials, placing them in a mold having an enclosed space or void shaped to produce shell 12, and closing the mold, with a very small opening for escape of air such as a slit of about 0.2 millimeters width. The amount of foamable material is typically sufficient to fill a volume greater than that of the finished earplug, so the material expands to the full size of the enclosed space within the mold and then presses with considerable pressure against the walls of the mold. Sufficient foamable material is present that the pressure of the expanding foam against the mold walls is typically at least 0.5 psi, and may preferably be about 2 psi for the embodiment of an earplug shown in FIG. 1. This provides for a thin shell made of dense to moderately dense foam. In one embodiment, a pour foaming process may be used.

The embodiment of FIG. 1 typically comprises gas-filled open cell foam. Applicant finds that the size of the cells within the pressure-molded earplug is greatest at the center of the earplug shell walls, and decreases at locations progressively closer to either the inner or outer surface of the earplug shell walls. Additionally, there tends to be more open cells near the center/middle of the shell body walls, with more closed cells near the inner and outer surfaces of the shell body so that the earplug typically forms a skin on the inner surface and the outer surface of the earplug shell where the pores are very small, and with most of the skin area being substantially closed cell. The open cells in the center of the shell body tend to provide a tortuous path that improves sound attenuation. The tighter cell structure at the surface tends to produce a more hygienic skin with stronger physical properties that may provide higher tear strength rating. As a result, there are few openings at the outer surface for picking up and retaining liquid and soiling material. Thus, such foreign material tends not to be absorbed into the earplug, so that the earplug's surface tends to remain clean and the lifetime of use of the earplug may be effectively extended. Also, the higher tear strength of the skin allows for one end of a cord to be embedded in the foam, which may be used to help keep the earplug pair together while ensuring that the cord does not interfere with fingertip insertion. Additionally, the denser skin allows for the surface to be wiped clean, which also helps extend the lifespan of the earplug. And the tighter skin tends to be smoother, aiding in insertion.

This skin is also smoother, more wetted-out, and denser than the inside of a shell that is formed by dip molding, and is also denser than the portions of the shell located towards the middle of the shell wall cross-section. Applicant finds that this results in a "flatter" attenuation of sound. Specifically, this embodiment of the earplug may provide improved attenuation at the difficult, lower frequencies. A flatter attenuation means that the percent of sound that is attenuated is more constant at different frequencies, such as in a range of 125 Hz to 4,000 Hz by way of non-exclusive example. In other words, the "flat" response of such an earplug means that the percentage of noise blocked by the earplug varies only slightly with the frequency of the sound (at least in the ranges a user would typically be exposed to in a moderately noisy environment). This embodiment may provide a flatter attenuation that does not vary as much as standard foam when attenuating across lower and higher frequency levels. Such flatter attenuation makes it easier for a worker to understand a supervisor who is shouting at him/her over a moderately noisy background environment, allowing for some level of verbal communication despite the usage of hearing protection.

Figure 3:
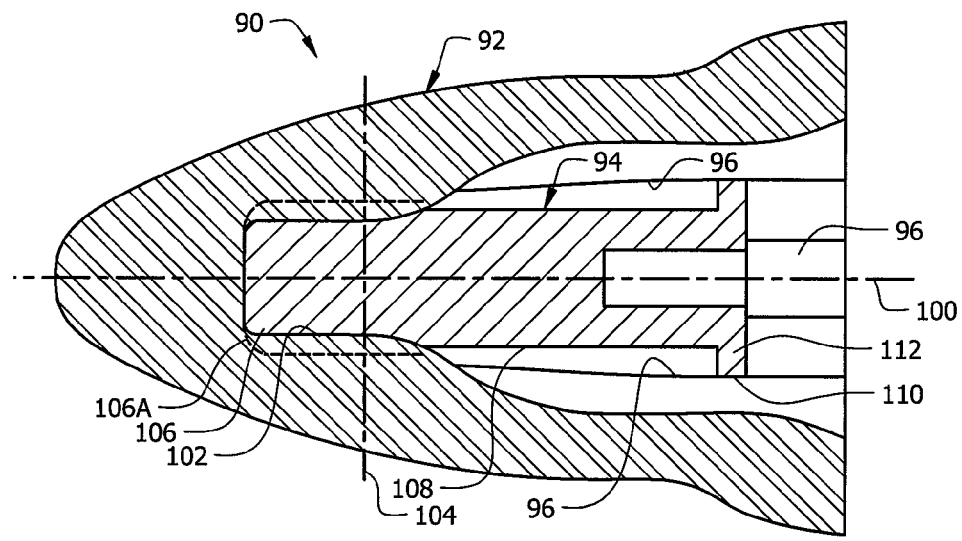
FIG. 3 is a cross-section drawing of another embodiment of an earplug.
Figure 10A:
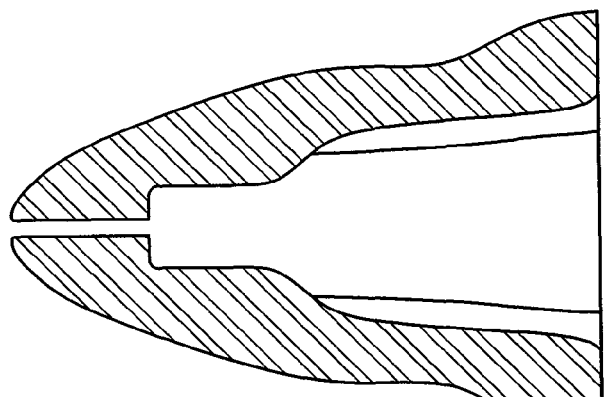
FIGS. 10A and 10B illustrate cross-section drawings of embodiments of an ear tip.
Figure 10B:
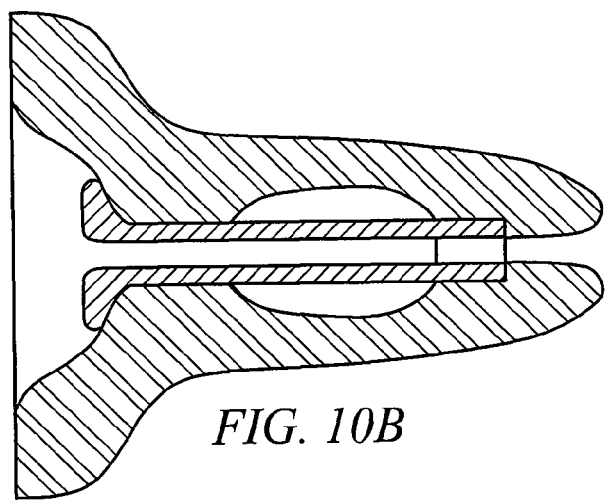

FIG. 3 shows another embodiment of the earplug 90 that includes a foam shell 92 and a stem 94. The shell has three splines 96 uniformly spaced about the earplug axis 100, and has a front passage portion 102 lying at and forward of the shell middle 104. The stem typically has a front end 106 that is larger in diameter than the pocket in the inside tip of the foam body 92. This provides for a basic press-fit retention of the stem in the pocket (although alternative embodiments might have the front end tip 106 of the stem bonded to the foam in the nose tip of the foam body 92). However, when the stem is pressed forward with a high enough force to elongate forward the front end of the foam shell, it has the effect of reducing the diameter of the foam body, making easier the insertion of the plug into the ear canal. The stem rear end has a flange 112 that lies in a sliding fit between the shell splines 96. The stem flange forms a larger rear end 110 that can serve as an effective contact surface to be pressed forward by a user's finger, and yet sound can pass around the flange and the rear and middle portions of the stem and between the shell splines. The stem flange may help limit the depth of insertion of the earplug 90 into a user's ear canal. In addition, the adjacent foam 111 at the base or rear of the earplug provides an additional limiter to over-insertion of the earplug. This may be a flared base, which may also provide a region to be grasped between thumb and forefinger in order to remove the earplug from the ear canal. The foam shell of FIG. 3 has a substantially occluded front end that may be completely closed in some embodiments (typically having a closed parabolic shaped tip when used as an earplug, for example), or it may have a small opening or channel allowing for sound transmission into the ear canal (as from the sound tube of a sound transmission device in the instance of an ear tip, as shown in FIGS. 10A and 10B for example).

The design of the embodiment of FIG. 3 may allow for improved fingertip insertion of the earplug. As FIG. 3 shows, the flange 112 on the rear end of the stem is inset or recessed from the rear end of the hollow shell body 92. This creates a rear pocket or recess that may serve as an effective receptacle for a fingertip. The combination of the flange in the rear of the stem and the rear recess may provide for improved fingertip insertion, offering users a great deal of control and precision in simple press-in insertion of the earplug into the ear canal. By way of example, the user may press and optionally twist with their fingertip to effectively navigate the curvature of the ear canal and comfortably insert the earplug for effective sound attenuation. This comfortable insertion is also enhanced by the compliant and flexible nature of the hollow shell body, along with the smooth skin on the foam body.

Applicant has designed and tested earplugs of the illustrated construction. The sample earplug 10 of the embodiment shown in FIG. 1 had a length along the axis of 0.85 inch, and a diameter at 120 of 0.6 inch. The thin-walled shell 12 of this test embodiment had walls of a thickness of about 0.06 inch at 122 at the splines, and a thickness of about 0.04 inch at 124 away from the splines. Applicant finds that wall thickness may typically vary from between about 0.040 to about 0.200 inch. The test earplugs had an overall NRR rating ranging from about 22 to about 29. The information regarding this sample is only exemplary, and is not intended to be limiting.

Figure 4:
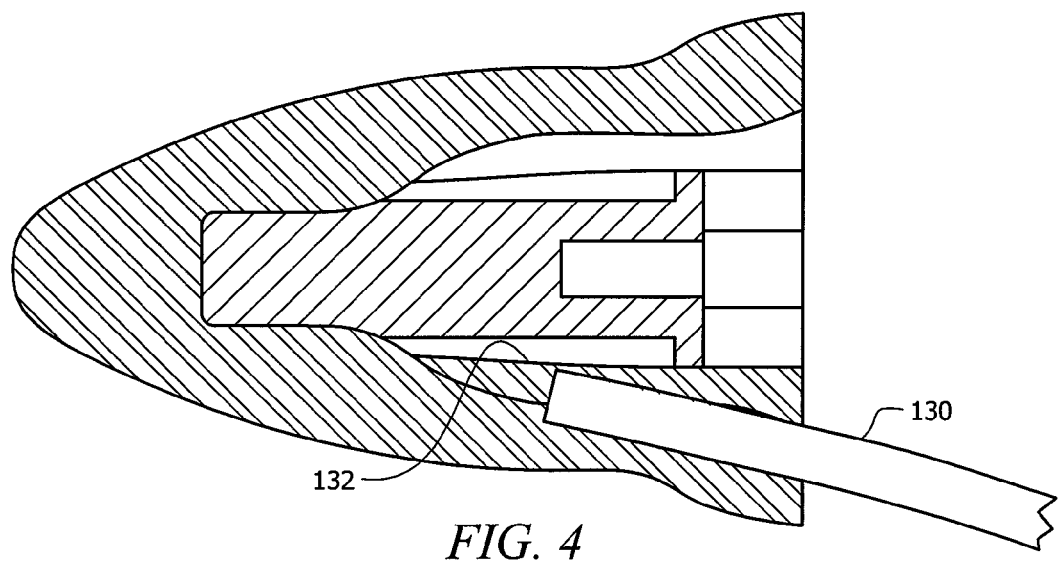
FIG. 4 is a cross-section drawing of another embodiment of an earplug having a cord.
Figure 9A:
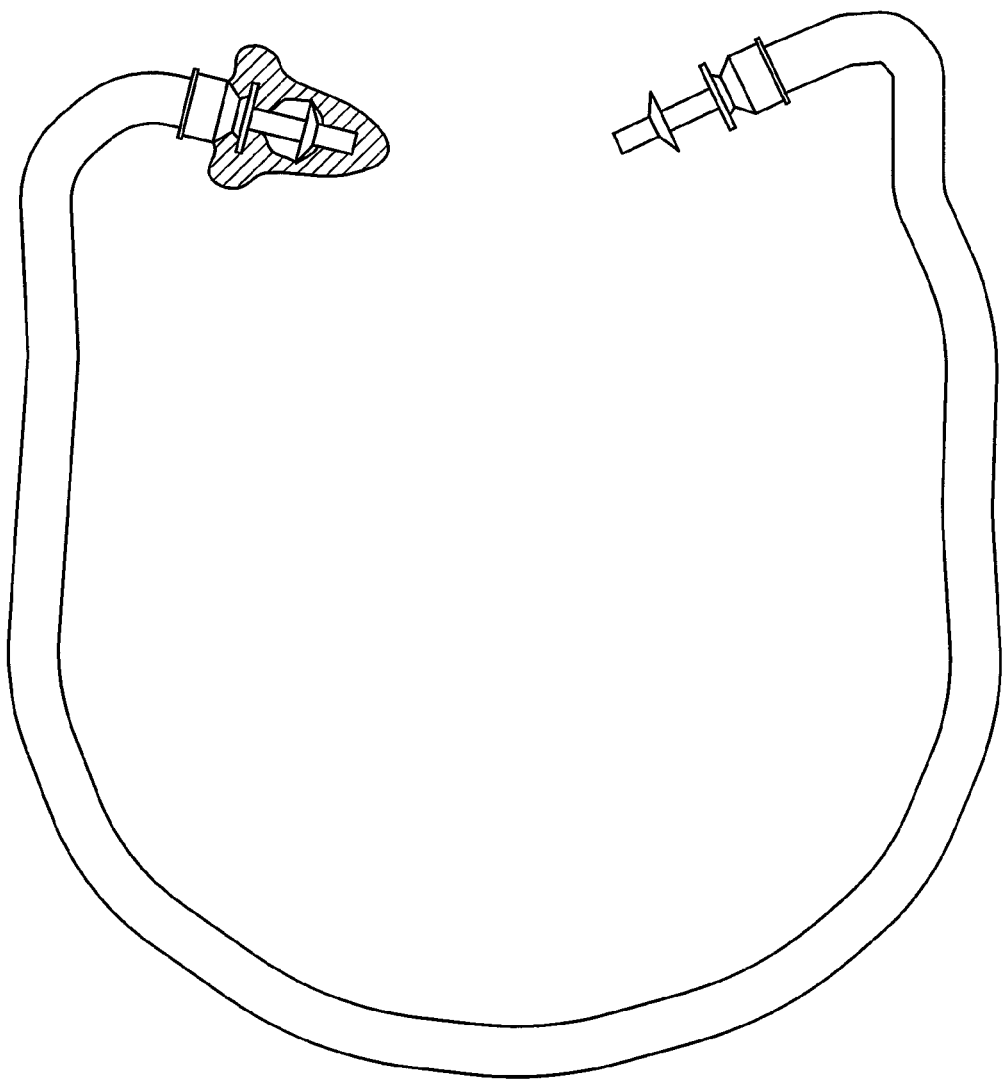
FIGS. 9A and 9B illustrate embodiments of banded earplugs, in which the foam hollow shell body of earplugs may be affixed to a retaining band that may incorporate the stem element.
Figure 9B:
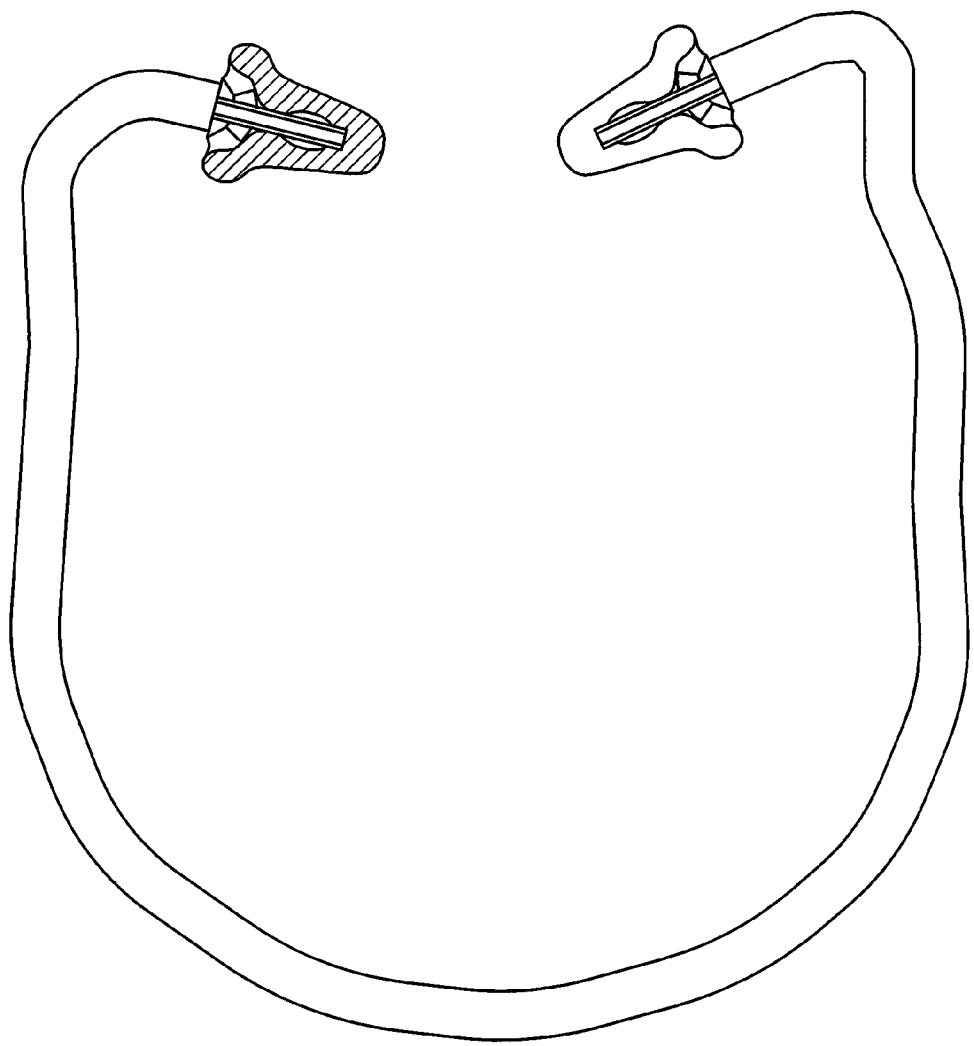

FIG. 4 shows an embodiment with the end of a cord 130 molded in place in one of the three splines 132 of the earplug. The cord may connect two earplugs (as shown in FIG. 13, for example) to keep the pair together and to allow a user to drape the earplugs (by the cord) around his/her neck. Thus, such a cord may improve the convenience of the earplugs for use in actual working environments. Embedding the cord in the foam shell body may be particularly helpful in this design, since it means that the cord need not be affixed to the stem. This improves fingertip insertion, since the cord will not interfere with fingertip contact with the stem in the rear recess. And it is noted that the thicker/denser/tighter skin may allow for the cord to be effectively embedded in the foam, since it has a higher tear strength rating. Optionally, an end (tip) of the cord may be placed in the mold, so that when the foamable materials are introduced into the mold, the earplug of FIG. 4 may be formed with a secure attachment to the tip of the cord. The other tip of the cord may be placed in a mold as well, so that a pair of earplugs are formed and are joined by the cord. In alternative embodiments, as shown for example in FIGS. 9A and 9B, a band may be used to join a pair of earplugs or earpods, with the stem being mounted onto the band. And in some embodiments, the stem(s) and band might be formed as a single unitary element. In this way, a pair of earplugs or earpods could be joined with a band to form a banded hearing protector.

Figure 6:
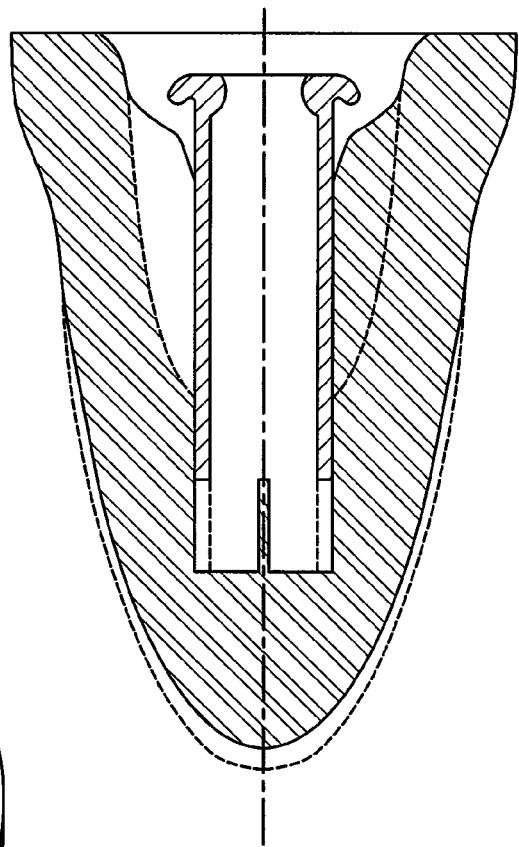
FIG. 6 is a cross-section drawing of the earplug embodiment of FIG. 5.
Figure 5:
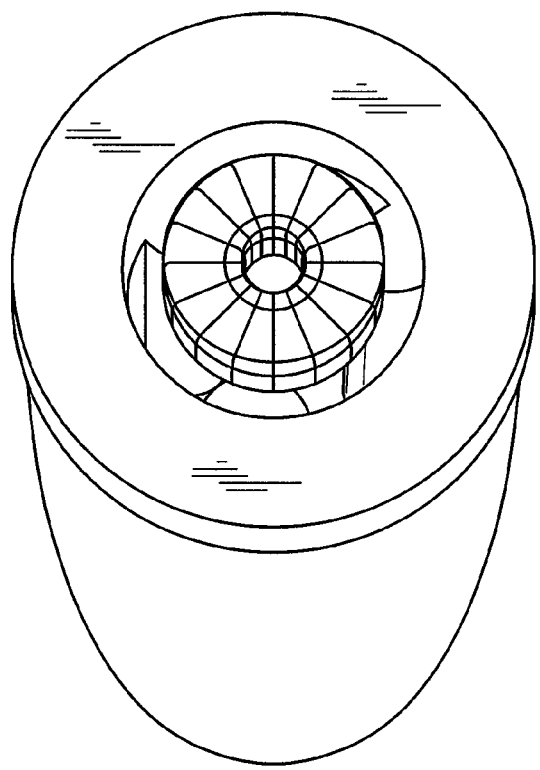
FIG. 5 is a perspective drawing of another embodiment of an earplug.

FIGS. 5 and 6 show another embodiment of the earplug 200 that includes a foam shell 202 and a stem 204. The shell has three splines 206 uniformly spaced about the earplug axis 210, and has a front passage portion 212. The stem of FIG. 6 is a tubular extruded insert having a front end 216 that has one or more slits 218 which make the tip of the stem front end relatively more flexible and conformable for an effective and easier insertion of the earplug 200 into the ear canal of the wearer. Using a hollow, tubular stem as the stiffener insertion stem provides for more flexibility of the earplug during insertion, thereby improving comfort. The hollow, tubular stem may provide sufficient vertical (columnar) compression rigidity to effectively aid in press-in insertion (by providing stiffer support to prevent columnar collapse of the soft foam and by elongating the shell and thereby reducing its diameter during fingertip insertion), while also providing sufficient flexibility in response to horizontal/radial bending forces (since a hollow tube is not as rigid as a solid cylinder, but is more prone to bending) to allow the earplug to more easily slide into place within non-linear ear canals. Providing one or more slits on the front end 216 of the tubular stem 204 may further improve comfort during insertion of the earplug of FIG. 6, since such slits may dampen the force of impact of the front end 216 by reducing the hoop strength of the front of the stem and allowing for some additional flex. The deeper portions of a user's ear canal have more sensitive nerves, and so are more likely to be irritated during insertion. So providing slits in the front portion of the stem may cause a noticeable improvement in user comfort without significantly impacting ease of insertion.

The stem rear end 208 of FIG. 6 also has a flange 214 that may be formed post extrusion. The stem flange forms a larger rear end 208 that can be pressed forward by a user's finger, and yet sound can pass around the flange and the middle portion of the stem and between the shell splines. The stem flange may help limit the depth of insertion of the earplug 200 into a user's ear canal. The stem flange may also provide a larger surface area to receive the user's fingertip during insertion, resulting in less pressure and better seating of the fingertip, thereby improving the ergonomic comfort and control features of the earplug. Other forms of post-extrusion stem modification may also be used in various embodiments. By way of non-exclusive example, radius forming on the front end of the stem may create a collapsed ball end, or stem wall zonal compression may be used to reduce the inner diameter of the stem at some selected midpoints along the stem's length or even to completely close off the hollow stem by crimping the hollow tube closed at some point along its length. Crimping the hollow stem of FIG. 6 partially or fully closed (such that the stem would be wasp-waisted) may alter the sound filtering characteristics of the stem (with low frequencies being blocked more effectively if the stem is crimped to about 0.015-0.040 inch internal diameter, for example), and thus the location and amount of crimp may be used to modify the sound attenuation properties of the earplug (resulting in a range of NRR ratings from about 20 through about 29). FIGS. 14A-14F demonstrate exemplary stems with various amounts, numbers, and locations of crimping along the length of the stem, along with various hole sizes in the flanged end of the stem. Crimping may provide a convoluted path that diffuses sound, and it may also increase flexibility of the stem, essentially acting as a hinge that may improve user comfort. Additionally, it may be possible to use multiple crimps at a plurality of locations along the length of the hollow stem to further modify the sound attenuation and/or user comfort provided by the earplug.

In one embodiment of FIG. 6, the hollow, tubular stem 204 may be filled at least partially with sound attenuating material. Such a configuration may also allow the hollow, tubular stem to provide for improved sound attenuation by minimizing the amount of sound resonating solid material located in the earplug that could serve to transmit sound deeper into the ear canal, and by replacing the removed solid material with foam having a high sound attenuation level. In one embodiment of FIG. 6, the hollow, tubular stem is placed in the mold for the foam shell prior to foaming of the materials to form the shell, and is oriented so that it will be properly located along the axis and so that the foamable materials may flow from the mold into the cavity of the hollow, tubular stem through at least one of its open ends. That way, when the foam shell is created, the foam materials may flow into at least one of the open ends of the tubular stem (typically the front end), thereby filling the stem with sound attenuating foam. And as noted above, the hollow stem may first be crimped to some degree at some point along its length, which may be used to alter the amount of foam that might fill the hollow stem (allowing further customization of the sound attenuation properties for the final earplug). If crimped partially closed, some amount of foam may flow past the narrower crimp (filling at least a portion of the hollow stem above the crimp without allowing the foam to flow out of the hollow stem), while completely crimping the hollow stem closed would effectively cap the amount of foam extending up the length of the hollow stem (with the portion of the stem above the crimp remaining free of foam).

Figure 11:
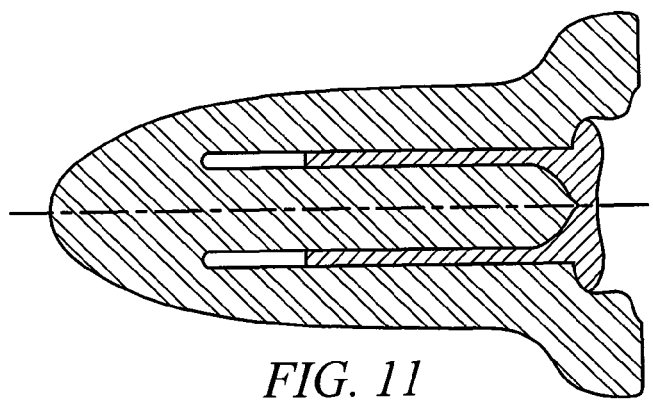
FIG. 11 is a cross-section drawing of an embodiment of an earplug in which foam back-flow fills the hollow stem.
Figure 12A:
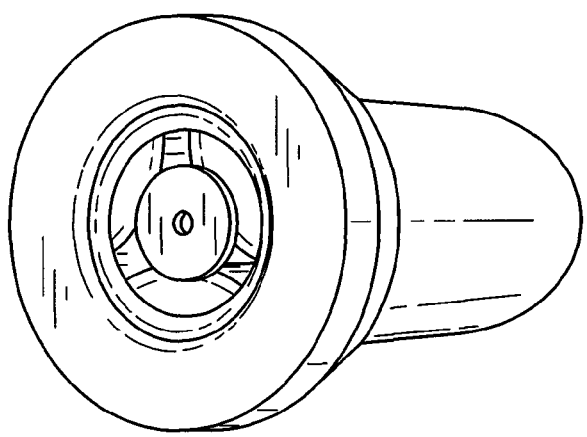
FIGS. 12A-12I are perspective drawings of another embodiment of an earplug.
Figure 12B:
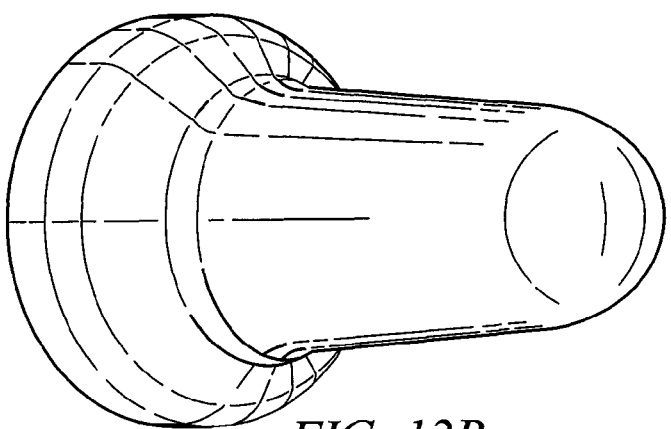
Figure 12C:
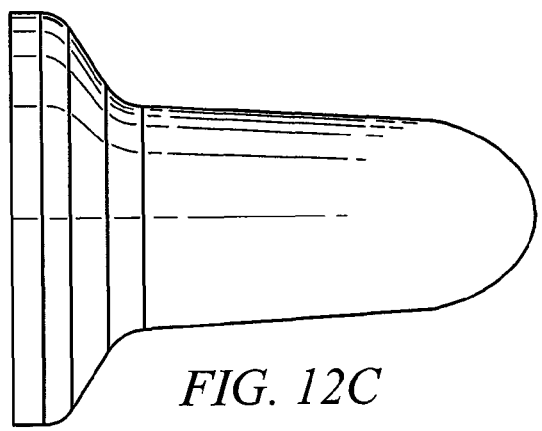
Figure 12D:
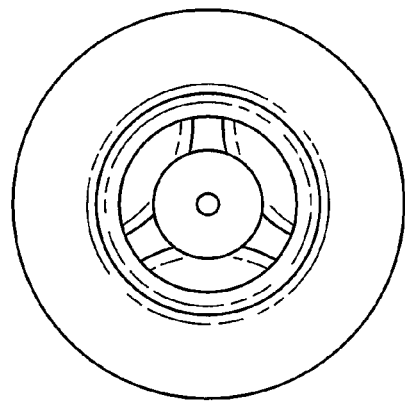
Figure 12E:
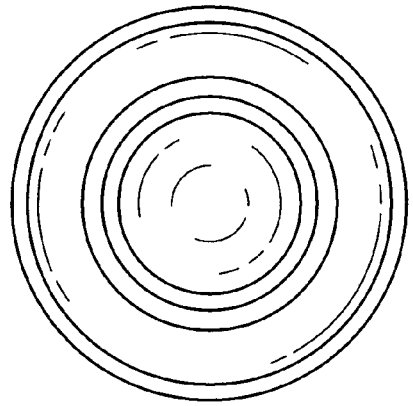
Figure 12F:
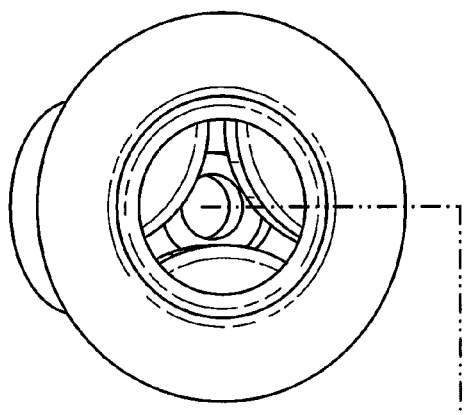
Figure 12F:
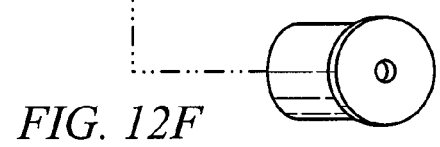
Figure 12G:
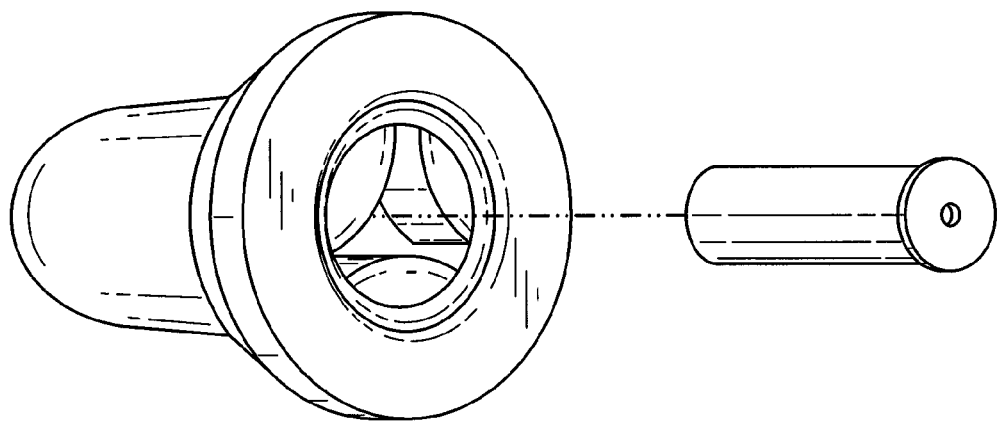
Figure 12H:
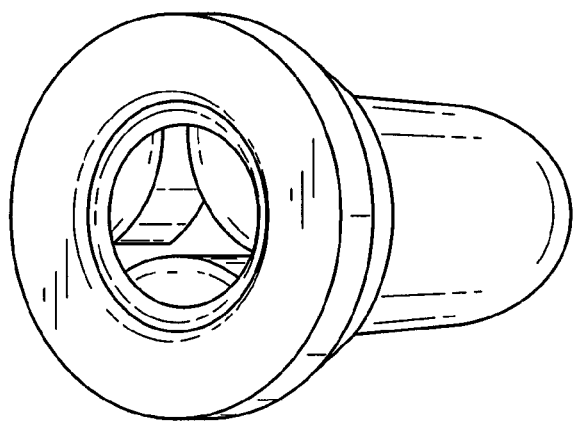
Figure 12I:
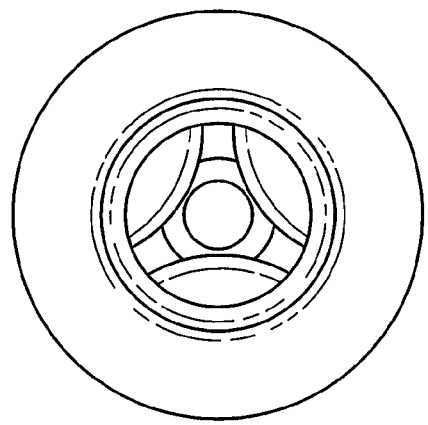
Figure 14A:
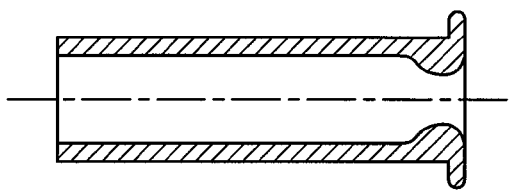
FIGS. 14A-14F are cross-section drawings of some possible embodiments of a stem.
Figure 14B:
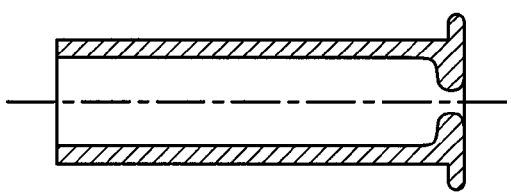
Figure 14C:
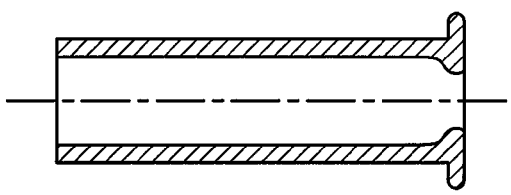
Figure 14D:
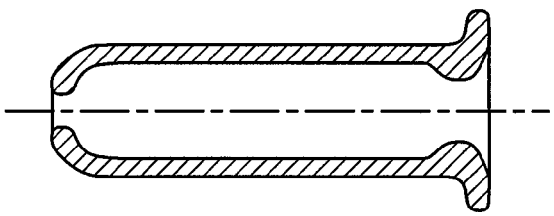
Figure 14E:
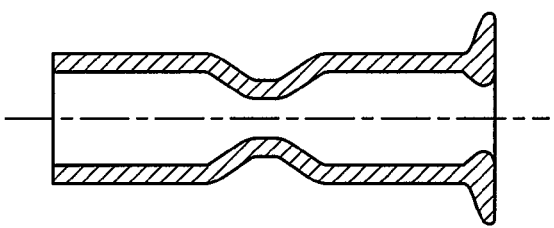
Figure 14F:
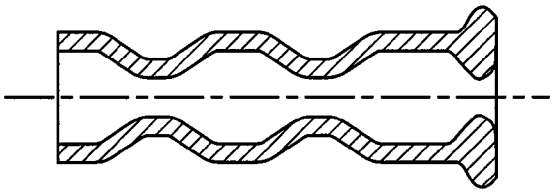

By way of example, the earplug of FIG. 6 may be formed by placing the stem in the cavity of a mold (shaped to form the shell), with the hollow cavity of the stem receiving a mandrel pin that is fixed to a front mold member (which is typically the lower mold member). The stem is fully slid forward into position in the mold. A quantity of foamable material is dispensed into the cavity of the mold, and the rear or upper mold member is closed and the foam material is allowed to solidify. The mandrel pin ensures that the sleeve is accurately centered in the foam shell. So the manufacturing process may optionally include any of the following steps: cutting tubular extrusion into lengths suitable for the sleeve, crimping the sleeve at least once at some point along its length, installing the sleeve in the mold by sliding it over a mandrel pin of the mold, positioning the sleeve within the mold so that when foamable materials fill the mold they will also flow into at least one open end of the hollow stem (which might result in an earplug embodiment as shown in FIG. 11, having foam back-flow into the hollow stem), dispensing foamable material into the mold, closing the mold, and later opening the mold and removing the earplug. Alternatively, the earplug could be formed using an open mold. In such an embodiment, the stem might be formed to include a skin-like surface that would contain the foam in the mold in order to form a hollow foam shell body having a central cavity. In such an embodiment, the second portion of the mold (formed by the skin-like surface) would become part of the earplug.

The shell and the stem may be formed of materials that allow for a secure chemical bond to each other when the foam of the shell solidifies while in contact with the stem. In one embodiment of FIG. 6, the foam shell is formed of FPU, while the stem is formed of TPU. This allows for chemical bonding between the two homologous (mutually chemically bonding) polymers during reaction of the foamable materials in the mold (as the FPU reacts with the TPU sleeve to form a strong chemical bond). This may result in improved sound attenuation (as the foam fills the cavity in the stem and provides a more unitary sound blocking earplug element), and provides greater integrity at the interface, which is the region that receives the greatest stress during insertion. The ability to chemically bond TPU may be enhanced by raising the surface energy of the polymer by such means as corona or plasma treatment, chemical priming, or surface etching to increase the surface contact, by way of non-exclusive example. Alternatively, solvent bonding and/or mechanical bonding (with flanges and/or cut-outs, by way of non-exclusive example) could be used to bond the stem in place within the shell.

Figure 7:
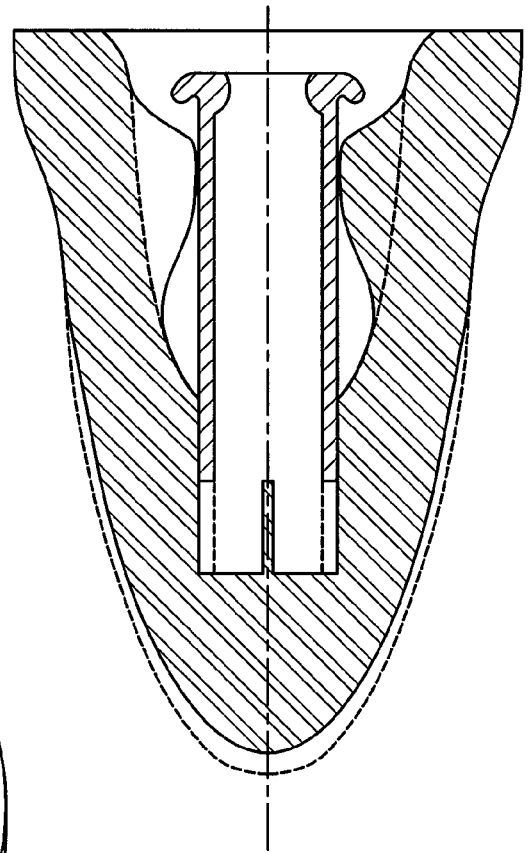
FIG. 7 is a perspective drawing of another embodiment of an earplug.
Figure 8:
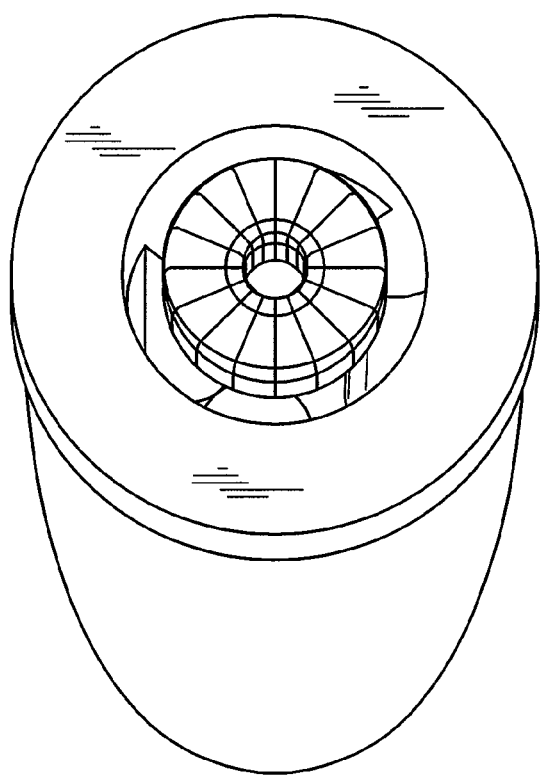
FIG. 8 is a cross-section drawing of the earplug embodiment of FIG. 7.

FIGS. 7 and 8 show another embodiment of the earplug 300 that includes a foam shell 302 and a stem 304. The shell 302 has a blind passage 306 that lies on the earplug axis 310, the passage having an open rear end 308 and a closed front end 312. The walls of the blind passage form a narrow neck 314 proximate the rear end 308 for retaining the stem 304 within the blind passage 306, the stem lying in a sliding fit in the narrow neck 314 of the passage. The stem is a tubular extruded insert having a front end 316 that has one or more slits 318 which make the tip of the stem front end relatively more flexible and conformable for an effective and easier insertion of the earplug 300 into the ear canal of the wearer. The stem rear end 319 has a flange 320 that is formed post extrusion. The stem flange forms a larger rear end 319 that can be pressed forward by a user's finger, and yet sound can pass around the flange and the middle portion of the stem. The stem flange helps limit the depth of insertion of the earplug 300 into a user's ear canal.

FIGS. 10A and 10B show exemplary ear tip embodiments. In these embodiments, while the front end is substantially occluded, it nevertheless comprises an opening or channel therethrough. This ear tip may be fit onto the sound tube of a sound transmission device (with the sound tube in this embodiment possibly taking the place of the stem; alternatively the sound tube could be used in conjunction with a mating hollow stem). The hollow body would then form a seal (designed to block out external noise that might interfere with the incoming sound signal), while allowing transmission of desirable sound signal through the channel toward the user's eardrum.

Applicant also notes that for such press-in (non-rolldown) EarTips, surface finish characteristics may be important to improve ease of insertion. Thus, it may be beneficial to provide an even smoother surface than provided by the dense skin of the polyurethane foam discussed in embodiments above, lowering the kinetic coefficient of friction to reduce resistance to insertion. Of course, it is also important that the static coefficient of friction not be reduced too much, so that the earplug will remain securely in place during usage (and will not back out and thus compromise the sound attenuation qualities of the earplug). Surface treatments with lubrication enhancing materials may help. It may also be beneficial to introduce such lubricity materials into the foam itself in the hopes of improving the insertion characteristics of the earplug, although cost factors may come into play. Applicant hereby incorporates by reference U.S. patent application Ser. No. 12/784,970 entitled "Improved EarTip" filed May 21, 2010 to the extent that it is not inconsistent with and/or does not contradict information presented directly in the present disclosure.

So in various embodiments, the invention may provide an earplug for a moderate noise environment (typically having flatter attenuation), which can be constructed at low cost, is sturdy, durably resists soiling and/or is easily cleaned for re-use, and is easy for even naïve, unsophisticated, and/or untrained users to install correctly in the ear canal (since no roll-down is required). In fact, the present invention provides for earplugs that are significantly lower in cost than typical reusable earplugs (so as to be competitive with standard single-use earplugs), but which may effectively have a longer lifespan allowing intermediate repeated reuse since they resist soiling better than typical single-use, disposable earplugs and allow for wiping and cleaning. Thus, the present earplugs essentially create a new category of intermediate long-term use earplugs with properties somewhere between the typical single-use, disposable earplugs and the more costly reusable earplugs currently on the market. The earplug may include a shell with a blind passage extending into its rear end, and a stem lying in the passage (cavity). The shell may optionally feature varying wall thicknesses, attenuation-enhancing baffles, splines, and/or internal restriction. The walls of the shell passage typically but optionally form a plurality of splines spaced circumferentially about the earplug axis and at least the rear part of the stem is guided in axial sliding by the splines. In one earplug embodiment, the stem is of constant cross section and lies in an interference fit in the shell and is held there by a shoulder formed in the splines. In another earplug embodiment, the stem front end lies in an interference fit with the shell and the stem rear end forms a flange that is slidable along the splines. Alternatively, the cavity in the shell body could be simple (with a smooth continuous inner surface for example), and the stem could have a complex outer shape (with projections or cut-outs for example). And in some embodiments, the front tip of the stem may be chemically bonded to the shell body. The shell is preferably molded of a polyurethane foam, which results in a skin on the inner and outer surfaces of the shell, increasing the hygiene, toughness and durability of the shell, while also providing for flatter attenuation. The comfort factor may also be improved by using a hollow, tubular stem (which may also be filled with foam to improve sound attenuation), which may also include one or more slits in its front end and/or may be crimped one or more times along its length. FIGS. 12A-12M illustrate an exemplary embodiment of such an earplug (and while the embodiment shown in these figures typically has a stem that is shorter than the hollow shell body, in other embodiments the stem may project out of the rear end of the hollow shell body).

While specific examples set forth above may relate to earplugs, it should be understood that this disclosure is not limited to such hearing protection applications. By way of example, the teachings could apply to various EarTips. The figures discussed above provide examples of various exemplary devices, systems, and techniques for providing flat attenuation moderate hearing protection, and ways to make and use such devices. These illustrations are merely exemplary. The scope of the present disclosure extends beyond the specific examples set forth above, capturing the full range of the inventive concept (and including all equivalents).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Accordingly, the scope of protection is not limited by the description set out above, but is defined by the claims which follow, that scope including all equivalents of the subject matter of the claims. Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings refer to a "Field of the Invention," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. The term "comprising" as used herein is to be construed broadly to mean including but not limited to, and in accordance with its typical usage in the patent context, is indicative of inclusion rather than limitation (such that other elements may also be present). In all instances, the scope of the claims shall be considered on their own merits in light of this disclosure, but should not be constrained by the headings set forth herein.

What is claimed is:

1. An earplug device comprising:
 a hollow body formed of open cell foam plastic material having an outside surface adapted to contact the surface of an ear canal, a substantially occluded front end, an open rear end, an inside surface and a central axis; and
 a stem of flexible material that is stiffer than the hollow body, located approximately along the central axis of the hollow body;
wherein:
 the hollow body encompasses a cavity;
 the stem comprises a front tip and a rear end;
 the rear end of the stein comprises a fingertip flange;

the stem is completely contained within the hollow body such that the rear end of the stem does not extend out of the open rear end of the hollow body;

the rear end flange of the stem is inset from the open rear end of the hollow body to form a recess in the rear end of the hollow body adapted to receive a fingertip for interaction with the flange, allowing for fingertip insertion of the earplug device;

the hollow body comprises three or more splines projecting into the cavity and contacting the stem to support the stem in place approximately along the central axis within the cavity; and the inside and outside surfaces of the hollow body comprise a substantially closed cell skin.

2. The device of claim 1 wherein the front tip of the stem is chemically bonded to the hollow body.

3. The device of claim 1 wherein the front end of the hollow body comprises a pocket, and the front tip of the stem is press-fit within the pocket.

4. The device of claim 1 wherein the stem comprises a hollow tube and wherein the front tip of the stem comprises at least one slit.

5. The device of claim 4 wherein the hollow tube of the stem is at least partially filled with foam plastic material.

6. The device of claim 4 wherein the stem is crimped at some midpoint between the front and rear ends, such that the stem is wasp-waisted.

7. The device of claim 1 wherein the front end of the hollow body comprises a parabola-shaped tip, and wherein the foam plastic material of the hollow body comprises open cell foam.

8. The device of claim 1 wherein the skin on the inside and outside surfaces of the hollow body has a thickness on the order of about one-twentieth millimeter, and is substantially continuous.

9. The device of claim 1 wherein the hollow body comprises polyurethane foam and the stem comprises TPE.

10. The device of claim 1 wherein the skin has a thickness on the order of approximately one-twentieth millimeter, is denser than the open cell foam forming the remainder of the hollow body, and is substantially continuous.

11. The device of claim 1 wherein the open cell foam provides flatter sound attenuation by offering improved attenuation at lower frequencies due to the skin.

12. The device of claim 1 wherein the stem comprises a front tip and a rear end; the front tip of the stem is chemically bonded to the hollow body; the rear end of the stem comprises a flange; the stem is completely contained within the hollow body such that the rear end of the stem does not extend out of the open rear end of the hollow body; and the rear end of the stem is inset from the open rear end of the hollow body to form a recess in the rear end of the hollow body adapted to receive a fingertip.

13. A method of forming an EarTip comprising the steps of:

extruding an elongated stem with a front end and a rear end;

placing the stem in a mold shaped to form a hollow shell body having an outside surface adapted to contact the surface of an ear canal and an inside surface encompassing a cavity;

providing foamable materials in the mold;

wherein:

the stem is placed so that it will be located approximately on the central axis of the hollow shell body and so that the stem is completely contained within the hollow body such that the rear end of the stem does not extend out of the open rear end of the hollow body;

the rear end of the stem comprises a flange;

the rear end flange of the stem is inset from the open rear end of the hollow body to form a recess in the rear end of the hollow body adapted to receive a fingertip for interaction with the flange, allowing for fingertip insertion of the earplug device;

providing foamable materials in the mold results in formation of the foam hollow body comprising a dense skin on the inside and outside surfaces.

14. The method of claim 13 wherein the stem comprises a hollow tube having a cavity therethrough, such that foamable materials enter the cavity of the stem when foaming in the mold.

15. The method of claim 13 wherein the stem and the hollow shell body are formed of homologous materials, such that a chemical bond forms between the hollow shell body and at least the front end of the stem.

16. The method of claim 15, wherein the stem is formed of TPU and the hollow shell body is formed of FPU.

17. The method of claim 14 further comprising forming a flange at the rear end of the stem and cutting at least one slit in the front end of the stem.

18. The method of claim 17 further comprising crimping the stem at some midpoint between the front and rear ends, such that the crimped midpoint restricts the flow of foamable materials through the cavity in the stem.

19. The method of claim 13 wherein the foamable materials form polyurethane foam; and the polyurethane foam is reaction molded under a pressure of at least about 0.5 psi in a closed mold.

20. An EarTip device comprising:

a hollow body formed of foam plastic material having an outside surface adapted to contact the surface of an ear canal, a substantially occluded front end, an open rear end, an inside surface and a central axis; and a stem of flexible material that is stiffer than the hollow body, located approximately along the central axis of the hollow body;

wherein:

the stem is shorter than the hollow body;

the stem comprises a front tip and a rear end;

the rear end of the stem comprises a fingertip flange;

the stem is completely contained within the hollow body such that the rear end of the stem does not extend out of the open rear end of the hollow body; and the rear end flange of the stem is inset from the open rear end of the hollow body to form a recess in the rear end of the hollow body adapted to receive a fingertip for interaction flange, allowing for fingertip insertion of the EarTip device.

21. The device of claim 20 wherein the foam plastic material comprises an open cell latex-modified polyurethane foam, and the inside and outside surfaces of the hollow body comprise a substantially closed cell skin.

22. The device of claim 20 wherein the stem and the hollow body are formed of homologous materials, and the stem and the hollow body are chemically bonded at least at the front tip of the stem.

23. The device of claim 20 wherein the hollow body comprises an odd number plurality of splines projecting into the cavity.

24. The device of claim 20 further comprising a cord having a tip, wherein the tip of the cord is embedded in the foam plastic material of the hollow body to securely attach the cord to the hollow body.

25. The device of claim 20 wherein the EarTip is an earplug.

* * * * *